United States Patent [19]

Davis

[11] Patent Number: 4,618,939
[45] Date of Patent: Oct. 21, 1986

[54] NUCLEAR DENSOMETER
[75] Inventor: James L. Davis, Marlow, Okla.
[73] Assignee: Halliburton Company, Duncan, Okla.
[21] Appl. No.: 513,528
[22] Filed: Jul. 13, 1983
[51] Int. Cl.$^4$ .............................................. G01T 1/16
[52] U.S. Cl. ................................ 364/555; 250/356.1; 364/558
[58] Field of Search ............................. 364/555, 558; 250/356.1; 376/246

[56] References Cited
U.S. PATENT DOCUMENTS 3,775,597 11/1973 November ........................ 364/558
4,292,433 8/1981 Löffel .............................. 250/356.1
4,480,311 10/1984 Mastain et al. ..................... 364/555

Primary Examiner—Errol A. Krass
Assistant Examiner—Heather R. Herndon
Attorney, Agent, or Firm—W. J. Beard

[57] ABSTRACT

A system for quickly indicating changes in density of a flow of material using a radiactive source and detector where the count rate indicative of density is processed for sensing significant changes in the density in the flow of material as distinguished from random changes and for producing an indication of such changes. In one aspect of the invention, a time filter is utilized with an RC circuit and diodes to require a count rate indicative of a significant density change before producing an indication. In another aspect of the present invention the count rate is processed with respect to a predetermined formulation to determine the occurrence of a significant density change in a time frame and for producing an indication when such change occurs.

7 Claims, 6 Drawing Figures

NUCLEAR DENSOMETER

BACKGROUND OF INVENTION

The present invention relates to nuclear densometers, and more particularly, to a method and apparatus for processing data to obtain a fast response to changes in the density of a fluid.

The prior art has developed digitally processed data for nuclear densometers, as illustrated by U.S. Pat. No. 3,657,532, issued to Carl W. Zimmerman. As set forth in the '532 Patent, digital systems allow the incorporation of extremely reliable, inexpensive and compact integrated circuits and can be used to develop digital pulse counting techniques. However, in the prior art, there remains a substantially long time response to a change in density in the fluid sample being tested and a consequence, a considerable volume of incorrect density fluid may be passed through the system for use before a correction in the density can be detected or made.

In oilwell cementing operations, the density of the cementing slurry is an important factor. The bore hole cementing fluid typically is a slurry of chemical constituents mixed with water and has a certain density. Should the composition of the slurry mixture change during the pumping operation, the density obviously changes and a change in mixture can affect the desired results in the cementing operation. For that reason, it is desirable to be able to quickly sense changes in density, i.e. changes in the mixture and to be able to provide a correction to the mixture before a large volume of incorrect mixture is introduced into the system.

Similarly, in fracturing of wells, monitoring of the density of the fracturing fluid is desirable.

It is accordingly a feature of the present invention to obtain a relatively quick response time to the change of density in a cementing or fracturing fluid system so that the fluid may be continuously monitored and corrected, if necessary to obtain a consistent density for the fluid mixture.

The present invention involves a method and system for sensing the density of a fluid for providing statistical count signals which are proportional to density and processing the count signals so that significant changes in density produce a quick response and indication of such change and so that statistical variations in the count signals are suppressed.

In one aspect of the present invention count signals are processed by a circuit means which has one or more fixed differential threshold detection levels so that the magnitude of the detected signals must exceed the fixed differential threshold level for a period of time. The circuit means utilizes an RC charging circuit with reversely connected diodes in series with the resistance so that when the forward voltage drops of a diode is exceeded, the capacitor is rapidly charged to produce an output signal. With more than one such circuit the range of response time can be expanded.

In another aspect of the present invention, count signals are processed by a computer to determine a relationship. When the count signals over a time period indicate a significant change in density an indication of such change is developed by using both a large and a small weighting factor. For random changes in density an indication is developed with a small weighting factor normally. The computer processes the count signals to ascertain the magnitude and duration of any changes in the count signal and upon meeting pre-set criteria produces an indication of the change.

THE DRAWINGS

A preferred embodiment of the invention is illustrated in the following figures in which.

DETAILED DESCRIPTION

Figure 1:
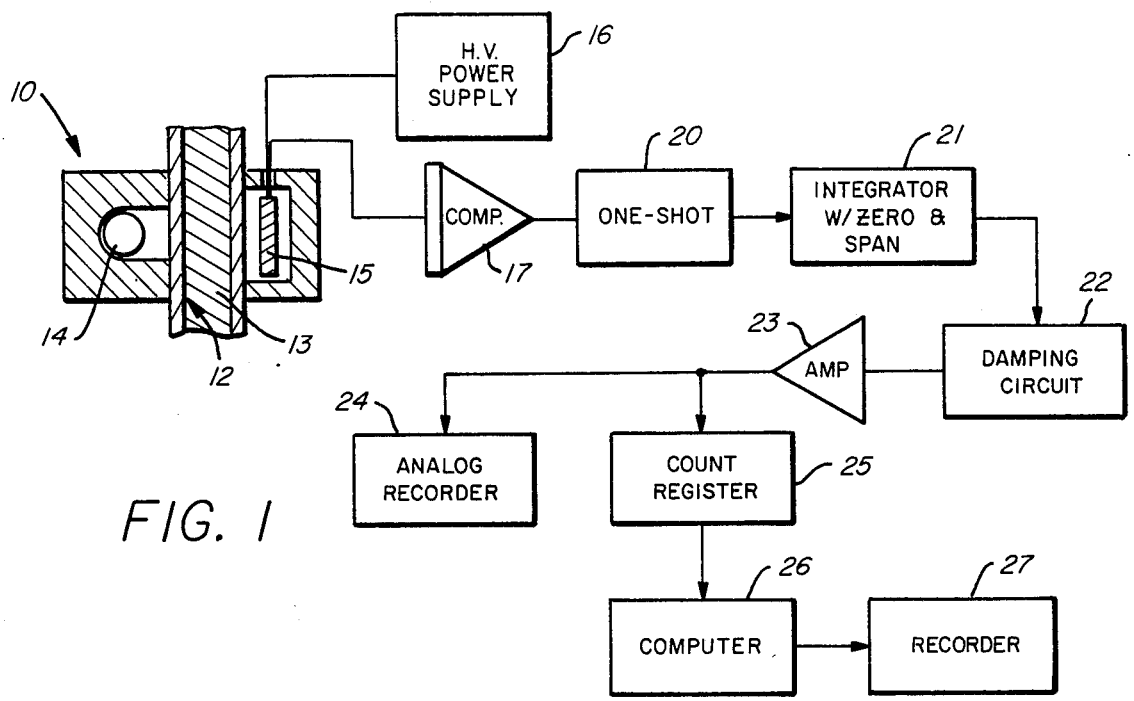
FIG. 1 is a schematic block diagram illustrating one embodiment of the present invention.

Referring now to FIG. 1, a housing 10 is mounted on a tubular pipe with a bore 12 through which a well cementing fluid 13 is caused to flow between cementing tanks or trucks (not shown) and a well bore to be cemented (not shown). A source of radiation 14 is located on one side of the bore 12 and, on an opposite side, a radiation detector 15 is located. The radiation provided by the source 14 is a constant intenisty over a long period of time (random intensity over a finite period) of gamma ray emissions. The gamma rays are transmitted through the material surrounding the bore 12, the slurry of cement 13 within the bore and to the detector 15. The detector 15 may be, for example, a crystal of sodium or cesium iodide (thallium activated) or other material capable of scintillating under irradiation and may include an electron photo multiplier tube for converting light flashes of the scintillation of the crystal into an electrical pulses. As will be apparent, the only variable with respect to density between the source 14 and detector 15 is the cement slurry 13. A percentage of the gamma rays emitted by the source 14 are absorbed or attentuated by the cement slurry 13 and do not reach the detector 15. Thus the counting rate of the output signal from the photo multiplier tube of the detector 15 is similarly related to the density of cement slurry 13 through which the rays must pass to reach the crystal in the detector 15 and the intensity of the source 14.

The detector 15 is powered by a high voltage power supply 16 and the output signals from the detector 15 are supplied to a comparator circuit 17. The comparator circuit 17 eliminates extraneous noise signals below a selected amplitude level determined by a reference level set by potentioner 17A, and amplifies the output signals which are passed through the circuit. The output of the comparator circuit 17 represents count pulses above the threshold level set by the comparator 17.

Figure 2:
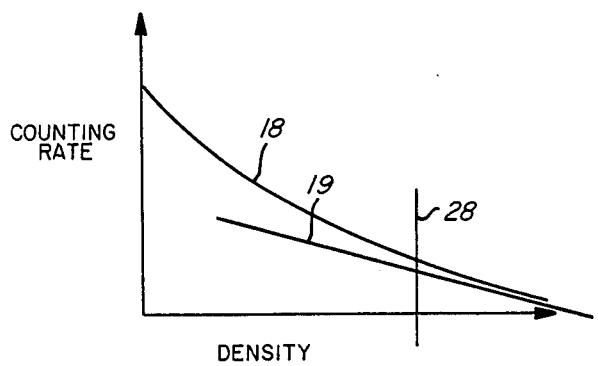
FIG. 2 is a graph illustrating density with respect to counting rate.

The output signals from the comparator 17 are applied to a one-shot 20 which linearizes the relationship of the comparator output as shown by the sloped line 19 in FIG. 2. Because of the dead time of the one-shot 20, the output frequency of one shot 20 is reduced more at the higher counting rates than at the low counting rates. The output of the one-shot 20 is supplied to an integrator 21. The output of the integrator 21 is supplied to a damping circuit or filter 22.

Figure 3:
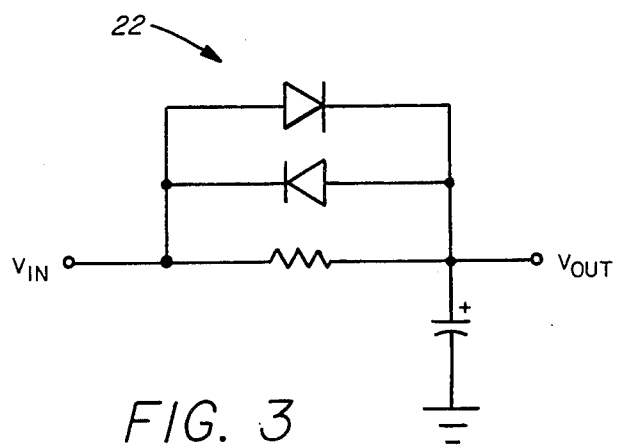
FIG. 3 is a schematic illustration of a damping circuit used in the system of FIG. 1.
Figure 4:
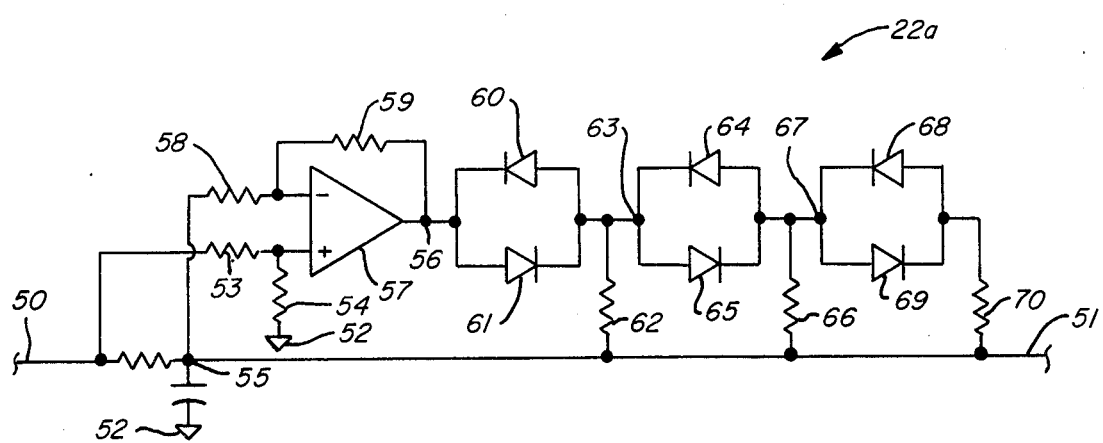
FIG. 4 is a schematic illustration of a modified damping circuit used in the system of FIG. 1.

The damping circuit 22, as shown in FIGS. 3 and 4 (FIG. 4 shows a multistage embodiment), includes an RC circuit with typical values of 100 K ohm resistance and 270 micro Farad capacitance and IN459A diodes reversely connected in parallel to the resistance. This configuration has a time constant of 27 seconds when the magnitude of the input voltage ($V_{IN}$) is less than ±0.75 volts. This corresponds to about ±0.75 pounds per gallon change in density. In other words, for random minor changes in density, the output is damped by the circuit thus indicating that the density of the slurry is nearly constant. The configuration also has a time constant of 0.59 seconds when the magnitude of the input voltage is greater than ±0.75 volts. This permits a faster output response of the circuit when a large change in density occurs.

The output of the damping circuit 22 is supplied to a Buffer amplifier 23 and then to an analog recorder 24.

Referring now to FIG. 4, a damping circuit 22a is illustrated in which the responsive time can be stepped or changed in proportion to the change in counting rates. In the circuit of FIG. 4, the RC circuit includes a resistance R connected in series between an input and output terminal 50, 51 and a capacitance C connected between the input terminal and a reference or ground 52. The input terminal 50 and one end of the resistance R is connected to the ground 52 via a pair of resistances 53, 54. The other end 55 of the resistance R is connected to the output 56 of an amplifier 57 via a pair of resistances 58, 59. The values of resistances 53 and 58 are made equal and the values of resistances 54 and 59 are made equal. The output 56 of the amplifier 57 is connected to a pair of reversely connected diodes 60, 61 which are, in turn, connected via a resistance 62 to the output terminal 51. The diodes 60, 61 are also connected at 63 to a second set of reversely connected diodes 64, 65. Diodes 64, 65 are connected via a resistance 66 to the output terminal 51 and also, at point 67, to a third set of reversely connected diodes 68, 69. The diodes 68, 69 are connected via a resistance 70 to the output terminal 51. The resistance values of resistances 62, 66 and 70 are an appropriate fraction of the value of the resistance R and are progressively smaller in value. Each of the sets of diodes provide a breakpoint. That is, when the voltage differential across the resistance R multiplied by the gain of the amplifier exceeds the forward voltage drop on the first set of diodes, a current flows through the resistance 62 to charge the capacitor C. The second and third breakpoints occur when the amplified voltage differential exceeds the forward voltage drops of the second and third sets of diodes. Thus, the response time is changed according to the voltage differential across the resistance R. The circuit reaches its steady state value fairly fast with a large step change on the input without any overshoot.

Figure 5:
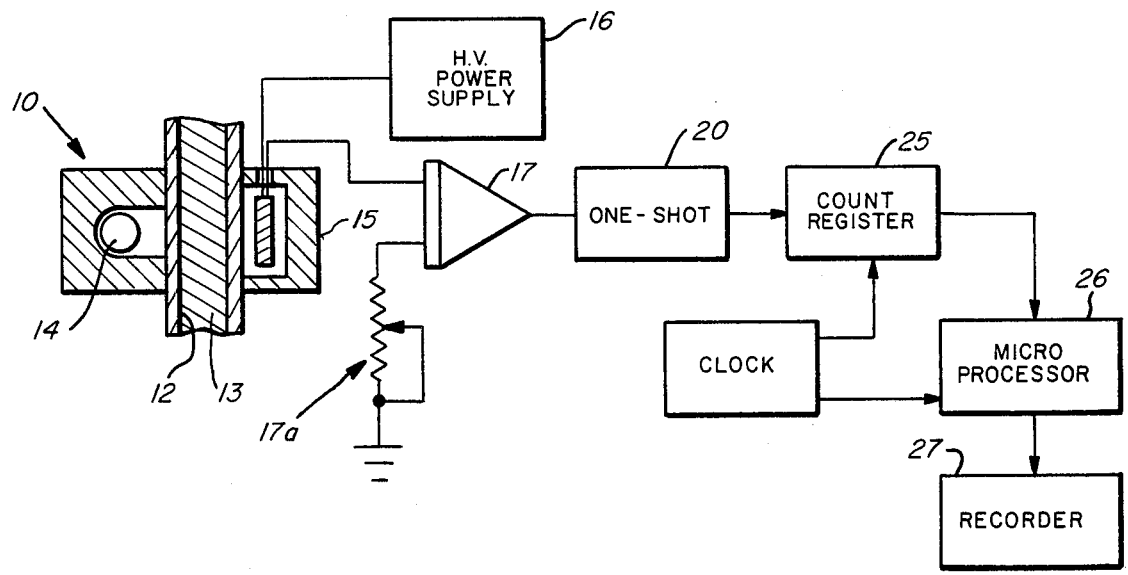
FIG. 5 is a schematic block diagram illustrating another embodiment of the present invention.

Referring now to FIG. 5, similar components to those illustrated in FIG. 1 are similarly numbered. In FIG. 5, the one shot 20 outputs to a counter register 25 and the counter register 25 outputs to a computer 26. The computer may be a ZYLOG 16 Bit microprocessor. The counter register 25 is keyed by (6) a clock 28 to systematically and regularly process the counts in the register 25 to the computer 26. The computer 26, upon processing of the data, provides an output to a recorder 27.

Before detailing the present invention in respect to processing of data by the computer 26, some background information may be helpful to an understanding of the present invention.

The number of pulses detected by the detector 15 may be shown to be:

$$N = S r_1 \ldots \quad (1)$$

Where N is the number of pulses counted during a time period S for randomly generated pulses from a detector and where the counting rate $r_1$ is related to the density of material.

For a fluid material having a given density, the following relationship exists:

$$N = K\, I\, e^{-\alpha t} \ldots \quad (2)$$

Where N is the number of pulses detected; K is a constant; $I\, e^{-\alpha t}$ is the activity of the source at time "t" for a decay factor $\alpha$.

The intensity I may also be stated to be:

$$I = I_k e^{-K/D(u/D)} \ldots \quad (3)$$

Where u/D is the mass absorption coefficient of the substance of the bore, $I_k$ is the radiation intensity at the detector with the bore empty, K is a constant dependent upon the width of the bore and D equals the density of the fluid material.

Rewriting equation 3 gives the following:

$$\frac{I}{I_K} e^{-K/D(u/D)} \quad (4)$$

A plot of the counting rate versus density is illustrated by the curve 18 in FIG. 2.

In the operation of the present invention, the detected counts are processed by the one shot 20 which produces a responsive output count signal to the count register 25 and to the computer 26 on a periodic basis. So long as the density of the slurry is constant, as shown by the vertical line 28 in FIG. 2, the count rate signal is processed using a relatively large weighting factor (32). However, if there is a large change in density, a small weighting factor (4) is used to process the count rate signal. The computer 26 samples the accumulated counts signals each tenth of a second and develops a smoothing variable or weighting factor. The smoothing variable or weighting factor is a function of the density of the slurry and if large changes of density occur for a sufficient period of time, then the smoothing variable or weighting factor is changed to provide an indication of the change in density.

Specifically, the computer 26 is programmed to determine the following:

$$\rho_{s,n} = \rho_{s,n-1} + \frac{1}{\tau}(\rho_{r,n} - \rho_{s,n-1}) \quad (5)$$

where
$\rho_{s,n} = n^{th}$ smoothed point value of sampled count rate data
$\rho_{r,n} = n^{th}$ raw data point value of current count rate data
$\tau =$ a weighting factor with one of two values dependent upon the following factors:
1. $\tau = 4$ if the absolute value of the difference between a new count rate and an old count rate average is equal to, or greater than, 1/128 of the old count rate average value for ten times in succession without a change in sign.

2. If $\tau$ is not 4, then the value of $\tau$ is set to 32.

If the raw count rate data is being processed for the first time, then a program step 44 sets a prior smoothed value "$\rho_{s,n-1}$" as equal to the raw count rate data value and the sign (SIGN$_1$) is set by a program step 45.

The difference "S" between the smoothed value and the raw data value is determined by a program step 46 where $$S = \rho_{r,n} - \rho_{s,n-1}$$

and (a) if this value exceeds zero (0), the program step 47 maintaines the sign positive and the absolute of the difference "S" is compared to the value of 1/128 $\rho_{s,n-1}$ in program step 30;

(b) if the difference value "S" is less than or equal to zero (0), the program step 48 changes the sign to negative and the absolute of the difference "S" is compared to the value of 1/128 $\rho_{s,n-1}$ in program step 30.

In the program, to initialize the program the sign is set to "1" (a positive value) in step 45 and in step 43, the program is set equal to zero (0) for the first time processing of data.

The service request step 41 is initiated by a clock 49 set to initiate requests at 0.1 second intervals.

In the program, if ten successive samples of accumulated count signals of the data $|(\rho_{r,n}-\rho_{s,n-1})|$ are equal to or greater than 1/128 $\rho_{s,n-1}$ and the sign (positive or negative) of does not change, then the weighting factor is set to a value of 4 in equation 5 which produces a faster indication of the change in density.

The weighting factor is set equal to 32 for any sample period when the output signal is indicative that no significant changes of density occurring.

Figure 6:
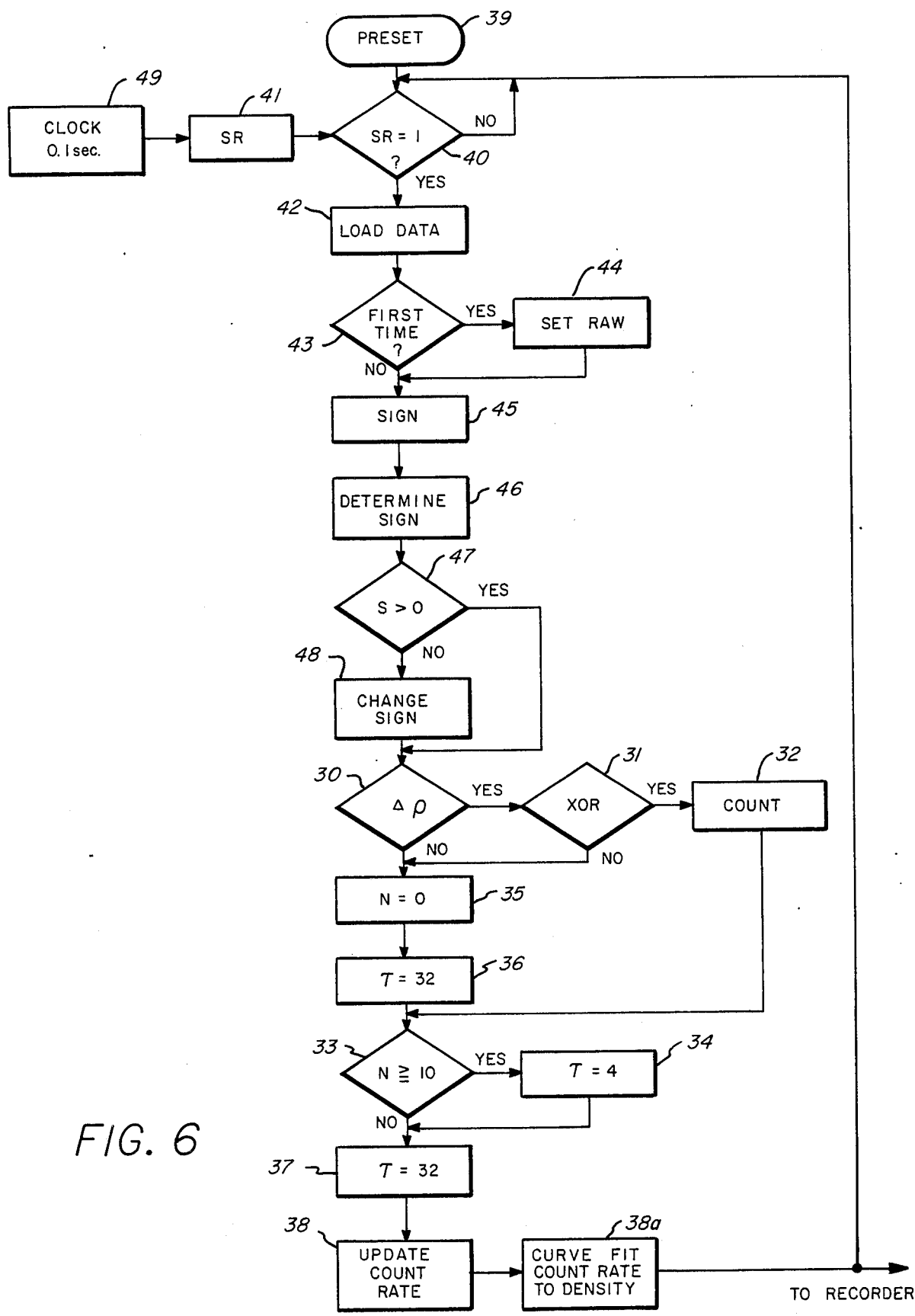
FIG. 6 is a schematic illustration of the flow chart for use with a microprocessor to process the data for obtaining fast response times and indications to changes in densities.

As shown in FIG. 6, the program for the computer 26 provides a fast response to changes in density. In the program the basis of the determination of a large change in density is upon a determination of the absolute value of "S" relative to a predetermined relationship which is expressed; (1)

$$|S| => \tfrac{1}{128} \rho_{s,n-1} \text{ or } |\rho_{r,n} - \rho_{s,n-1}| => \tfrac{1}{128} \rho_{s,n-1}$$

where $\rho_{r,n}$ is the raw data value of count rate $\rho_{s,n-1}$ is the old smoothed data value of count rate preceding an nth raw data value.

This determination as shown in the program step 30 of the flow chart.

(2) If the absolute value of $|\rho_{r,n}-\rho_{s,n-1}|$ exceeds, or is equal to, 1/128 $\rho_{s,n-1}$ or "yes", then the program follows to an "exclusive or" gate 31 which determines the sign (positive or negative) of the absolute value. If the sign of the absolute value is the same as the sign of the immediately preceding absolute value ("yes") then the counter 32 value is incremented by one (N=N+1) which counts the number of successive times of this occurrence without a change of sign (positive or negative) occurs. If the sign does not change, and the counter 32 value (N) is equal to ten (10) or greater, then this determination by the program step 33 ("yes") sets a weighting factor ($\tau$) to four (4) in the program step 34. If the sign changes, or S is less than 1/128 $\tau_{s,n-1}$ then N is set to zero (0) in 35 and the weighting value is also set equal to thirty-two (32) in a program step 36.

(3) The program utilizes either the weighting value of 4 or 32 as the case may be, sets SIGN$_2$ equal to SIGN$_1$ (positive or negative) at step 37 and determines the new smoothed value at step 38 by the relationship $$\rho_{s,n} = \rho_{s,n-1} + \tfrac{1}{\tau}(\rho_{r,n} - \rho_{s,n-1})$$

where $\tau_{s,n}$ = the new smoothed value $\tau_{s,n-1}$ = the old smoothed value $\tau_{r,n}$ = the new raw data value.

The new or updated smoothed value $\tau_{s,n}$ is curve fitted to the count rate curve 18 (See FIG. 2). When this is complete then the result is converted to a density representation prior to display on the recorder supplied to recorder circuitry and also recycled in the program to the output of point 39. The program is in a loop at step 40 until a service request occurs at program step 41, the raw data (count rate value) is loaded into the program by the program step 42. Upon loading of the raw data, the program step 43 determines if the raw data is appearing for the first time in the program.

While this system is particularly adapted to the measurment of a cement slurry where extremely good resolution of density measurement is required along with good accuracy and high stability, other adaptations and advantages of the invention will be readily apparent to one skilled in the art to which the invention pertains from a reading of the foregoing. It is accordingly intended that the foregoing description be illustrative only and that the scope of the invention be limited only by the language, with a full range of equivalents, of the appended claims.

I claim:

1. A method for use in a system utilizing a radioactive source and detector collimated to pass radiation through a flow of fluid for monitoring the density of such fluid, comprising the steps of:

detecting radiation passed through a flow of fluid and developing electrical signals representative of the detected radiation, processing said electrical signals with respect to a predetermined time and magnitude function parameter to provide an output response signal whenever said electrical signals simultaneously attain both the time and magnitude function parameter of said predetermined parameter whereby random electrical signals which do not attain said predetermined time and magnitude function parameter do not significantly affect an output response signal.

2. The method as defined in claim 1 wherein said predetermined time and magnitude function parameter has a range established by a resistance-capacitance circuit with the resistance of said RC circuit connected to a plurality of resistances and reversely connected diodes so as to provide different time functions as a function of the magnitude of said electrical signals.

3. The method as defined in claim 1 wherein said predetermined time and magnitude function parameter is established by comparison of presently occurring electrical signals to preceding electrical signals which exceed a predetermined magnitude over a period of time for producing said output response signal.

4. The method as defined in claim 1 wherein said comparison is based upon a determination of the amount of change in magnitude of said electrical signals.

5. In an apparatus for utilizing a radioactive source and detector collimated to pass radiation through a flow of fluid, the improvement comprising
- means for producing first electrical signals in response to radiation passed through a fluid from a source of constant radiation intensity where the rate of occurrence of said electrical signals to a predetermined magnitude are proportionally related to the density of the fluid; and
- means for processing said electrical signals including a plurality of series connected stages of reversely connected diodes and resistances connected across the resistance of a resistance-capacitance circuit whereby the occurrence of output response signals are a function of the magnitude of said electrical signals.

6. In an apparatus for utilizing a radioactive source and detector collimated to pass radiation through a flow of fluid, the improvement comprising
- means for producing first electrical signals in response to radiation passed through a fluid from a source of constant radiation intensity where the rate of occurrences of said electrical signals of a predetermined magnitude are proportionally related to the density of the fluid; and
- computer means for processing said electrical signals having a means for determining the relationship of a preceding density value to a present density value and for producing a response when the absolute value of said present density value exceeds the absolute value of said preceding density value for a predetermined successive number of times.

7. The apparatus according to claim 6 wherein the means for determining the relationship of a preceding density value to a present density value determines the following relationship:
- preceding density value plus the number one divided by a factor number times the difference between present density value and the preceding density value where the factor number is a large number if there is a significant change in density of the fluid.

* * * * *